United States Patent
Pinkos et al.

(10) Patent No.: US 9,923,194 B2
(45) Date of Patent: Mar. 20, 2018

(54) PROCESS FOR PURIFYING N-ALKYLPYRROLIDONES

(71) Applicant: BASF SE, Ludwigshafen (DE)

(72) Inventors: Rolf Pinkos, Bad Duerkheim (DE); Thomas Vogler, Ludwigshafen (DE); Karl Ott, Plankstadt (DE)

(73) Assignee: BASF SE, Ludwigshafen Am Rhein (DE)

( * ) Notice: Subject to any disclaimer, the term of this patent is extended or adjusted under 35 U.S.C. 154(b) by 0 days.

(21) Appl. No.: 15/017,864

(22) Filed: Feb. 8, 2016

(65) Prior Publication Data

US 2016/0156022 A1 Jun. 2, 2016

Related U.S. Application Data

(62) Division of application No. 14/084,888, filed on Nov. 20, 2013, now Pat. No. 9,255,069.

(60) Provisional application No. 61/729,347, filed on Nov. 22, 2012.

(51) Int. Cl.
| | |
|---|---|
| C07D 201/16 | (2006.01) |
| C07D 207/267 | (2006.01) |
| H01M 4/04 | (2006.01) |
| H01M 4/139 | (2010.01) |
| C07D 207/273 | (2006.01) |
| C07D 207/263 | (2006.01) |

(52) U.S. Cl.
CPC ........ H01M 4/139 (2013.01); C07D 207/263 (2013.01); C07D 207/273 (2013.01); H01M 4/04 (2013.01)

(58) Field of Classification Search
CPC ... C07D 201/16; C07D 207/267; H01M 4/04; H01M 4/139
USPC ........................................................ 548/555
See application file for complete search history.

(56) References Cited

U.S. PATENT DOCUMENTS

| | | | |
|---|---|---|---|
| 4,965,370 A | 10/1990 | Goetz et al. | |
| 2005/0010057 A1 | 1/2005 | Rudloff et al. | |
| 2013/0150591 A1 | 6/2013 | Pinkos et al. | |

FOREIGN PATENT DOCUMENTS

| | | |
|---|---|---|
| EP | 2602247 A1 | 6/2013 |
| JP | 03014559 U | 8/1995 |
| JP | 10310795 A | 11/1998 |
| JP | 11071346 A | 3/1999 |
| JP | 11349566 | 12/1999 |
| JP | 2001354769 A | 12/2001 |
| JP | 2004284958 A | 10/2004 |
| JP | 2007099690 A | 4/2007 |
| KR | 101134663 B1 | 4/2012 |
| WO | WO-03/053924 A1 | 7/2003 |
| WO | WO-2010057917 A1 | 5/2010 |

OTHER PUBLICATIONS

U.S. Appl. No. 61/567,657.
U.S. Appl. No. 61/567,681.

*Primary Examiner* — Matthew Coughlin
*Assistant Examiner* — Sagar Patel
(74) *Attorney, Agent, or Firm* — Drinker Biddle & Reath LLP

(57) ABSTRACT

Process for purifying N-alkylpyrrolidones which due to a previous use comprise at least one of the impurities of the formula I or II

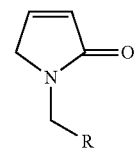

I

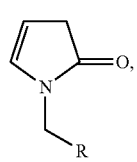

II where R is hydrogen or a C1-C20-alkyl group,
wherein
a basic compound is added to the N-alkylpyrrolidone to be purified and the temperature of the mixture is at least 80° C. not more than 20 minutes after addition of the basic compound and
N-alkylpyrrolidone is distilled off from the mixture obtained.

8 Claims, No Drawings

PROCESS FOR PURIFYING N-ALKYLPYRROLIDONES

CROSS-REFERENCE TO RELATED APPLICATIONS

This application is a divisional application of U.S. application Ser. No. 14/084,888 filed Nov. 20, 2013, from which benefit is claimed under 35 U.S.C. §120. U.S. application Ser. No. 14/084,888 claims benefit under 35 U.S.C. §119(e) of U.S. Provisional Application Ser. No. 61/729,347, filed Nov. 22, 2012, and which both applications are incorporated herein by reference in their entirety The present invention relates to a process for purifying N-alkylpyrrolidones which due to a previous use comprise at least one of the impurities of the formula I or II

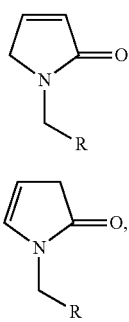

where R is hydrogen or a C1-C20-alkyl group.

In this process,
a basic compound is added to the N-alkylpyrrolidone to be purified and the temperature of the mixture is at least 80° C. not more than 20 minutes after addition of the basic compound and
the N-alkylpyrrolidone is distilled off from the mixture obtained.

The present invention further relates to a process for the use, purification and reuse of N-alkylpyrrolidones, wherein
a) a polymer is dissolved in an N-alkylpyrrolidone,
b) electrodes of lithium ion accumulators are produced using this polymer and a contaminated N-alkylpyrrolidone comprising at least one of the impurities of the formula I or II

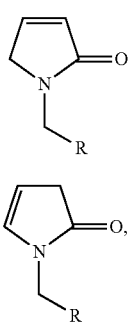

where R in formulae I and II is hydrogen or a C1-C20-alkyl group, is recovered, c) a basic compound is added to the recovered N-alkylpyrrolidone and the temperature of the mixture is increased to at least 80° C. not more than 20 minutes after addition of the basic compound,
d) the N-alkylpyrrolidone is distilled off from the mixture obtained and
e) is reused as solvent for the production of electrodes for lithium ion accumulators.

BACKGROUND OF THE INVENTION

Polymers are frequently used for producing lithium ion accumulators, e.g. as polymer electrolyte or for producing electrodes, it is usual to use, for example, polyvinylidene fluoride for producing the electrodes.

For this purpose, polyvinylidene fluoride is usually dissolved in an organic solvent and a suspension is produced by addition of lithium storage materials and optionally conductive additives. The electrode is obtained by coating a support, for example a metallic support, with this suspension and subsequently removing the solvent, N-Alkylpyrrolidones, in particular N-methylpyrrolidone, have been found to be suitable solvents.

The solvent can be contaminated as a result of the above use. The coating process introduces impurities, and by-products of the solvent used are also formed as a result of the high temperatures required and/or the presence of oxidizing compounds, in the case of N-methylpyrrolidone (NMP), compounds of the above formulae I and II, where R is an H atom, are formed by undesirable secondary reactions. These compounds have a boiling point similar to that of NMP and are therefore very difficult to separate from NMP by distillation.

Only solvents having a high purity and freedom from water can be used for producing long-lived lithium ion accumulators. A solvent which has been used once can only be reused when it has been purified and once again meets the demanding requirements in respect of purity and freedom from water.

JP 11071346 and JP 10310795 disclose purifying NMP which has been used as solvent for polyvinylidene fluoride by addition of acidic compounds, in particular by contact with acidic solids.

WO 2010/057917 describes the purification of NMP which has been used as solvent for polyvinylidene fluoride and the production of lithium ion accumulators. The purification is effected by addition of activated carbon, and the process is therefore a purification by adsorption.

The addition of alkali metal hydroxides or alkaline earth metal hydroxides to NMP has also already been described. Thus, distilling NMP in the presence or alkali metal hydroxides or alkaline earth metal hydroxides in order to prevent the formation of peroxides and stabilize the NMP is known from JP 2004284958 and JP 2007099890.

U.S. Pat. No. 4,965,370, JP 2001354769 and JP 11349566 describe the purification of NMP which has been used in the preparation of polyarylene sulfide; impurities from the polyarylene sulfide process can in each case be removed by addition of alkali metal hydroxides or alkaline earth metal hydroxides and the NMP can be reused for this process.

JP 03014559 discloses the removal of N-methylsuccinimide and phenol from NMP by addition of metal hydroxides or metal carbonates. Hare too, the NMP concerned is from the polyarylene sulfide process.

WO 03/053924 describes a process for preparing NMP from gamma-butyrolactone and methylamine. Here, metal hydroxides are used to remove excess gamma-butyrolactone by salt formation.

It was an object of the present invention to provide a process for purifying previously used N-alkylpyrrolidone, in particular NMP, which allows the reuse of the N-alkylpyrrolidones for any applications. In particular for the production of lithium ion accumulators. The process should be very simple and effective. Impurities of the above formulae I and II which have been introduced or formed should ideally be removed completely by the process.

We have accordingly found the process defined above.

DETAILED DESCRIPTION OF THE INVENTION

The process of the invention is a process for purifying N-alkylpyrrolidones which have already been used at least once. For example, the N-alkylpyrrolidones could have been used as solvents.

The N-alkylpyrrolidones concerned are preferably N-alkylpyrrolidones of the formula A

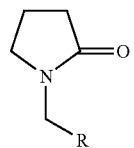

A where R is hydrogen or a C1-C20-alkyl group.

In particular, R in formula A is hydrogen or a C1-C3-alkyl group, and R is particularly preferably hydrogen or a methyl group. If R is hydrogen, the compound concerned is N-methylpyrrolidone (NMP), and if R is a methyl group, the compound concerned is N-ethylpyrrolidone (NEP). Particular preference is given to NMP or NEP. Very particular preference is given to NMP.

As a result of the previous use, the N-alkylpyrrolidone comprises at least one of the impurities of the formula I or II

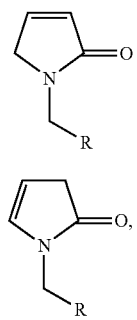

I

II where R is hydrogen or a C1-C20-alkyl group.

The compounds of the formula I and II are isomers which frequency occur in admixture. The N-alkylpyrrolidone to be purified can therefore comprise both compounds. R is preferably hydrogen or a C1-C4-alkyl group.

When the N-alkylpyrrolidone to be purified is NMP, R in formulae I and II is hydrogen.

When the N-alkylpyrrolidone to be purified is NEP, R in formulae I and II is a methyl group.

The content of compounds of the formulae I and II in the N-alkylpyrrolidone can be, in particular, from 0.0005 to 1 part by weight per 100 parts by weight of N-alkylpyrrolidone, in the present process, particular preference is given to using an N-alkylpyrrolidone having a total content of compounds of the formulae I and II of from 0.0005 to 0.5 part by weight, particularly preferably from 0.0005 to 0.1 part by weight, per 100 parts by weight of N-alkylpyrrolidone.

Apart from the compounds of the formulae I and II, the N-alkylpyrrolidone to be purified can comprise further organic compounds as impurities.

Further organic compounds which can be comprised as impurity are, for example, those of the following formulae

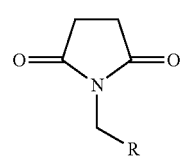

III

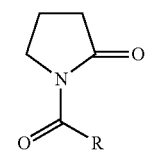

IV

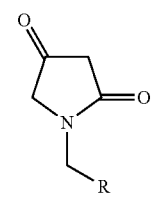

V

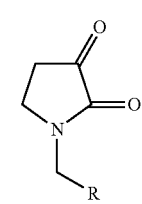

VI

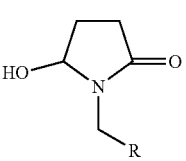

VII

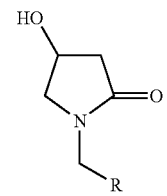

VIII

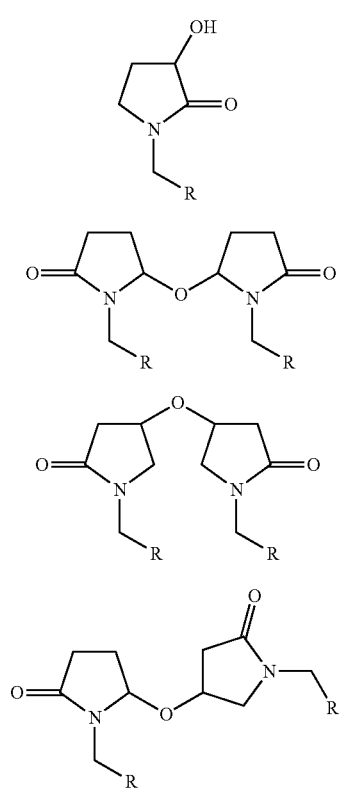

where R is in each case hydrogen or a C1-C20-alkyl group.

Apart from the compounds of the formulae I, II and possibly III to XII, the N-alkylpyrrolidone to be purified can comprise further organic compounds which originate from the production process for the N-alkylpyrrolidone and are not counted as impurities. Apart from gamma-butyrolactone and the amine used for preparing the N-alkylpyrrolidone (methylamine in the case of NMP), these further organic compounds are derivatives of N-alkylpyrrolidone which are substituted by alkyl radicals on the ring carbons. Preferred alkyl radicals are methyl and ethyl groups and can be present either individually or as a mixture on all ring carbons. The content of the substituted N-alkylpyrrolidones is generally less than 1 part by weight, in particular less than 0.5 part by weight, per 100 parts by weight of N-alkylpyrrolidone. The content of gamma-butyrolactone generally less than 0.1 part by weight. In particular less than 0.05 part by weight, per 100 parts by weight of N-alkylpyrrolidone. The content of the amine used for preparing the N-alkylpyrrolidone is generally less than 0.005 part by weight, in particular less than 0.003 part by weight, per 100 parts by weight of N-alkylpyrrolidone.

The N-alkylpyrrolidone to be purified generally comprises a total of from 0.0005 to 5 parts by weight, in particular from 0.0005 to 2 parts by weight, of organic compounds of the formulae I to XII as in impurities per 100 parts by weight of N-alkylpyrrolidone.

The N-alkylpyrrolidone to be purified can further comprise water or can be present in admixture with water. Large amounts of water can have been introduced by previous uses.

The N-alkylpyrrolidone to be purified can therefore have, for example, the following composition
100 parts by weight of N-alkylpyrrolidone,
a total of from 0.0005 to 5 parts by weight of organic compounds of the formulae I to XII as impurities and from 0.01 to 200 parts by weight of water.

In particular, the N-alkylpyrrolidone to be purified can have the following composition
100 parts by weight of N-alkylpyrrolidone
a total of from 0.0005 to 2.5 parts by weight of organic compounds of the formulae I to XII as impurities and from 0.1 to 100 parts by weight of water.

A basic compound is added to the N-alkylpyrrolidone to be purified, in the following, the term basic compound also encompasses mixtures of various basic compounds.

The basic compound is preferably a compound which in an amount of 5 parts by weight in 100 parts by weight of water (at 20° C., 1 bar) gives a pH of at least 8, particularly preferably at least 9. In the above definition, it is not necessary for the 5 parts by weight of the basic compound to dissolve completely in water; the critical thing is merely that the pH increase occurs after addition of the basic compound.

The basic compound can be organic or inorganic compounds. Possibilities are, for example, alkali metal hydroxides, alkaline earth metal hydroxides, alkoxides, carbonates, carboxylases, complex hydrides, ammonia or amines. Mention may be made by way of example of LiOH, NaOH, KOH, $Mg(OH)_2$, $Ca(OH)_2$, $Ca(HCO_3)_2$, $CaCO_3$, sodium oxalate, sodium borohydride, lithium aluminum hydride, sodium methoxide, sodium ethoxide, potassium methoxide, potassium ethoxide and the alkylamine corresponding to the N-alkyl-substituted pyrrolidone.

Particular preference is given to inorganic compounds, in particular bases comprising alkali metal or bases comprising alkaline earth metal.

The basic compound added is very particularly preferably NaOH, KOH, sodium methoxide or potassium methoxide.

In a particularly preferred embodiment, the basic compound is sodium hydroxide.

The basic compound can be added as such or as a solution to the N-alkylpyrrolidone to be purified. If the basic compound is added in solution, the solvent can be, for example, water or organic solvents, e.g. the respective N-alkylpyrrolidone or mixtures of the respective N-alkylpyrrolidone with water.

The basic compound is preferably used in amounts of from 0.01 to 10 parts by weight per 100 parts by weight of the N-alkylpyrrolidone to be purified (sum of N-alkylpyrrolidone and all organic constituents present therein, e.g. impurities and derivatives). It is particularly preferably used in amounts of from 0.01 to 1 part by weight and very particularly preferably in amounts of from 0.01 to 0.5 part by weight, in particular from 0.05 to 0.5 part by weight, per 100 parts by weight of the N-alkylpyrrolidone to be purified.

Not more than 20 minutes, preferably not more than 10 minutes, particularly preferably not more than 5 minutes, very particularly preferably not more than 2 minutes, after addition of the basic compound, the temperature of the resulting mixture of N-alkylpyrrolidone to be purified and basic compound is at least 80° C.

The temperature is preferably at least 100° C.

The above temperature can easily be set by
combining the basic compound and the N-alkylpyrrolidone to be purified and quickly heating the mixture obtained so that the necessary temperature is reached within the prescribed time (alternative 1) or preheating the N-alkylpyrrolidone to be purified so that the desired temperature prevails immediately after addition of the basic compound (alternative 2).

A particular embodiment of alternative 2 is addition of the basic compound directly during the distillation by means of which the purified N-alkylpyrrolidone is separated off.

Without the above temperature increase, solid can easily precipitate. A disadvantage of this is that, for example, pipes and valves car, become blocked, which makes it necessary for the plant to be shut down and requires appropriate cleaning.

N-Alkylpyrrolidone is distilled off from the mixture. The purified N-alkylpyrrolidone is preferably taken off at the top of the column.

The distillation is preferably carried out at a temperature of from 50 to 350° C., particularly preferably from 100 to 250° C., and a pressure of from 0.3 to 5 bar.

Suitable columns for the distillation are columns known to those skilled in the art. Preference is given to packed columns, tray columns having sieve trays, columns having dual-flow trays, columns having bubble capped trays or rectification columns equipped with valve trays, dividing wall columns or thin film and falling film evaporators.

The distillation is preferably carried out in the absence of oxygen. For the present purposes, absence means that the proportion by volume of oxygen is less than 0.1%. In particular less than 0.01% and very particularly preferably less than 0.001%, based on the total volume of the distillation column.

The addition of the basic compound to the N-alkylpyrrolidone is preferably carried out under an inert gas atmosphere so that the oxygen content is reduced during the entire process. Preference is given to carrying out the entire process in the absence of oxygen, with absence of oxygen meaning a proportion by volume of oxygen of less than 0.1%, in particular less than 0.01% and very particularly preferably less than 0.001%, based on the total volume of the apparatus part utilized in the particular case (vessel, distillation column).

The apparatuses used are preferably made of stainless steels, likewise all pipes and column internals.

The process can be carried out batchwise or continuously.

When it is carried out batchwise, the basic compound can be added to an initial charge of N-alkylpyrrolidone to be purified and the resulting mixture can be distilled batchwise.

The process is preferably carried out continuously.

For this purpose, the starting materials, i.e. the basic compound and the N-alkylpyrrolidone to be purified, are combined continuously. They can, for example, be fed continuously into a reservoir and be mixed there; the distillation can be supplied continuously from this reservoir.

The basic compound and the N-alkylpyrrolidone to be purified can be fed as separate streams directly and continuously to the distillation.

The N-alkylpyrrolidone to be purified is preferably fed into the stripping section of the column. The basic compound can be introduced as pure substance or as solution on any tray of the distillation column.

The distillation cart be carried out in one or more stages, i.e. in one or more columns.

A dividing wall column, for example, is also suitable for a single-stage, continuous distillation.

In a preferred embodiment, a continuous, two-stage distillation is carried out.

For this purpose, the N-alkylpyrrolidone to be purified (preferably NMP to be purified) and the basic compound (preferably NaOH) can be fed, either in admixture or separately, to a first distillation column. In the first distillation column, low boilers such as methylamine, in particular water, are preferably separated off at the top at a temperature at the bottom of from 150 to 250° C., in particular from 180 to 250° C., and a pressure of from 0.1 to 5 bar, in particular from 0.3 to 3 bar, in the second distillation column the bottoms from the first distillation column can be purified by distillation under reduced pressure, for example at a temperature at the bottom of from 80 to 180° C., in particular from 100 to 160° C., and a pressure of from 0.005 to 0.5 bar, in particular from 0.01 to 0.3 bar. The purified N-alkylpyrrolidone can be separated off as a side offtake stream from the second column and the bottoms, which comprise impurities and the basic compound or reaction products thereof, can be discharged continuously.

A particular embodiment of the process comprises carrying out the distillation of the N-alkylpyrrolidone to be purified in admixture with additional N-alkylpyrrolidone from the production process.

N-Alkylpyrrolidone, in particular NMP, can be obtained by reaction of gamma-butyrolactone with the corresponding amine (methylamine in the case of NMP). This reaction gives a product stream composed of N-alkylpyrrolidone (NMP), wafer, unreacted starting materials (gamma-butyrolactone and methylamine) and possibly by-products. This product stream is worked up by distillation. The N-alkylpyrrolidone to be purified can be mixed in any amount with this product stream. The N-alkylpyrrolidone to be purified can comprise the basic compound even before being combined with the product stream. As an alternative, it is naturally also possible to add the basic compound to the product stream, and in this case the basic compound is added to the N-alkylpyrrolidone to be purified only by mixing with the product stream.

After the distillation, the purified N-alkylpyrrolidone comprises, per 100 parts by weight of N-alkylpyrrolidone.
 a total of less than 0.5 part by weight of the impurities III-XII
 less than 0.05 part by weight of water and
 a total of less than 0.01 part by weight of compounds of the formulae I and II.

In particular, the purified N-alkylpyrrolidone comprises, per 100 parts by weight of N-alkylpyrrolidone,
 a total of less than 0.1 part by weight of the impurities III-XII
 less than 0.03 part by weight of water and
 a total of less than 0.0005 part by weight of compounds of the formulae I and II.

The purified N-alkylpyrrolidone comprises, in particular, less than 5% by weight, preferably less than 1% by weight, particularly preferably less than 0.1% by weight, of the total amount of the compounds of the formulae I and II originally comprised in the contaminated N-alkylpyrrolidone.

The purified N-alkylpyrrolidone obtained is, due to its high purity, once again suitable for the production of electrodes for lithium accumulators.

EXAMPLES

The following examples serve to illustrate the invention. The contents of impurities indicated in the examples have been determined by gas chromatography (GC instrument HP6890, FID detector, nitrogen carrier gas at 1.0 mL/min (const. flow); Split Ratio 1:50; column RTX-1, 30 m, 0.32 mm, 1.0 μm film; temperature program; start at 80° C., then 5° C./min to 140° C., then 5° C./min to 200° C. and 10 min isothermal, then 10° C./min to 340° C. and 8 min isothermal). Water values were determined by Karl-Fischer titration. NMP and the respective impurities were used as indicated in the examples. All working steps were carried out in cleaned apparatuses under a nitrogen atmosphere; the absence of foreign compounds was monitored by GC before commencement of the experiments.

Comparative Example 1

A contaminated NMP comprising 0.5% of water and 0.031% of impurities of the formulae I-XII (impurity of the formulae I and II, 0.004%; impurity of the formula III, 0.017%; impurity of the formulae IV-VI, 0.003%; impurity of the formulae VII-IX, 0.002%; impurity of the formulae X-XII, 0.005%) was admixed with 0.1% of NaOH (calculated as pure NaOH, used as 30% strength aqueous solution) and pumped into a tank. After a residence time of 4 hours at a temperature of 15° C., about 100 kg of a precipitate precipitated from an initial amount of 23.5 metric tons of NMP. For the subsequent two-stage distillation, the contents of the tank were continuously conveyed via a riser tube in an amount of 500 L/h into the first valve tray column (40 trays, inlet on tray 21) and the feed stream was stopped after introduction of 23.3 metric tons, so that the solid remained in the tank. The distillation was carried out at temperatures at the bottom in the range from 180 to 185° C., a pressure at the top of the column of 530 mbar and a reflux to offtake ratio of about 1:1. The bottoms from the column were conveyed into the second valve tray column (40 trays, inlet on tray 21) and distilled at temperatures at the bottom in the range from 165 to 170° C. and a pressure at the top of the column of 220 mbar, with the product being taken off at the top. The sodium content of the feed to the second valve tray column was in the range from 0.0005 to 0.001%; the distillate continued to have the impurities of the formulae I and II in an amount of 0.002% and impurity of the formula IV-VI in an amount of 0.001% and was free of the impurity of the formula III; the distillation yield was 90% and the water content of the product was 0.005%.

Comparative Example 2

A contaminated NMP comprising 1.0% of water and 0.074% of impurities of the formulae I-XII (impurity of the formulae I and II, 0.003%; impurity of the formula III, 0.035%; impurity of the formulae IV-VI, 0.002%; impurity of the formulae VII-IX, 0.032%; impurity of the formulae X-XII, 0.002%) was admixed with 0.1% of NaOH (calculated as pure NaOH, used as 30% strength aqueous solution) and pumped into a container. About 0.1 kg of a precipitate precipitated from an initial amount of 30 kg of NMP within a residence time of 8 hours at a temperature of 25° C. For the subsequent distillation, the contents of the container were transferred into the pot of a distillation apparatus and fractionated batchwise. The solid remained in the container. The distillation was carried out in a column (Sulzer CY Packung, 13 lengths of 0.63 m, 1 of 0.30 m) having a runback divider at temperatures at the bottom in the range from 130 to 140° C. and pressures in the range from 1000 mbar (low boiler removal) and 90 mbar at the top at a reflux to offtake ratio of 50:1. A total of 30 distillate fractions were taken off. The first five fractions obtained at temperatures at the top of 55-118° C. comprised predominantly water (>98%). The subsequent fractions 8-24 (altogether about 21 kg) were obtained at 100 mbar and a temperature at the top of 122-128° C. These comprised water in an amount of less than 0.1%, NMP in purities above 99.8% but still the impurities of the formula I and II, 0.001% and of the formulae IV-VI, 0.001%, present in the initial charge. From fraction 25 (altogether about 4 kg), the undesirable impurities of the formulae I-XII could no longer be detected by GC analysis: the distillation yield was 13% and the water content of the product was 0.005%.

EXAMPLES ACCORDING TO THE INVENTION

Example 1

The feed mixture from comparative example 1 was admixed continuously with 0.1% of NaOH (calculated as pure NaOH, used as 30% strength aqueous solution) by means of a static mixer at a residence time of 30 seconds at a feed rate of the contaminated NMP of 500 liters (l)/hour (h) and a temperature of 15° C. This feed stream was, in contrast to comparative example 1, introduced directly into the first valve tray column (inlet of tray 21) and heated there to above 150° C. within 2 minutes. The formation of a solid was not observed. The distillation was carried out in two stages in a manner analogous to comparative example 1. The sodium content in the feed to the second valve tray column was in the range from 0.05 to 0.06%, the distillation yield was 90%, the impurities of the formulae I-XII could no longer be detected in the product by GC analysis and the water content was 0.005%.

Example 2

The feed mixture from comparative example 2 was mixed with 0.1% of NaOH (calculated as pure NaOH, used as 30% strength aqueous solution) by means of a static mixer at a residence time of 30 seconds and heated to 95° C. within 10 minutes by means of a preheater, with formation of a solid not being observed. The mixture was transferred at a feed rate of 5 l/min into the pot of a distillation apparatus and directly fractionated batchwise in a manner analogous to comparative example 2 (heating to 130° C. within a further 20 minutes). A total of 20 distillation fractions were taken. The first five fractions obtained at temperatures at the top of 55-118° C. comprised predominantly water (>98%). The subsequent fractions 6-20 (altogether about 25 kg) were obtained at 100 mbar and a temperature at the top of 122-126° C. These comprised water in an amount of less than 0.1%, NMP in purities above 99.8% and the undesirable impurities of the formulae I-XII could no longer be detected by GC analysis. The distillation yield was 83% and the water content of the product was 0.005%.

Example 3

The feed mixture from comparative example 2 was mixed with 0.15% of potassium methoxide (KOMe for short, calculated as pure KOMe, used as 25% strength methanolic solution) by means of a static mixer at a residence time of 30 seconds and heated to 95° C. within 10 minutes by means of a pressure-resistant preheater, with formation of a solid not being observed. The mixture was transferred at a feed rate of 10 l/min into the pot of a distillation apparatus and directly fractionated batchwise in a manner analogous to comparative example 2 (heating to 130° C. within a further 20 minutes). A total of 20 distillation fractions were taken. The first five fractions obtained at temperatures at the top of 55-118° C. comprised predominantly water (>98%) and a small proportion of methanol. The subsequent fractions 6-20 (altogether about 25 kg) were obtained at 100 mbar and a temperature at the top of 122-126° C. These comprised water in an amount of less than 0.1%, NMP in purities above 99.8% and the undesirable impurities of the formulae I-XII and methanol could no longer be defected by GC analysis.

Example 4

The feed mixture (500 milliliters) from comparative example 1 was heated with 1% of monomethylamine (calculated as pure amine, used as 40% strength aqueous solution) to 100° C. in a steel autoclave over a period of 15 minutes and then heated further at 200° C. for 6 hours, with a pressure of about 20 bar being built up. The solids-free reaction output was subsequently distilled in a laboratory apparatus (standard distillation setup with Vigreux column) under conditions analogous to comparative example 2. About 90% of NMP in the desired purity (monomethylamine content <0.002%) were obtained, with the predominant part of the remainder being contaminated only by water contents which were too high (>0.1%).

The invention claimed is:

1. A process for producing electrodes comprising;
a) dissolving a polymer in an N-alkylpyrrolidone,
b) producing electrodes of lithium ion accumulators using the polymer dissolved in the N-alkylpyrrolidone, wherein the producing of the electrodes provides N-alkylpyrrolidone contaminated with at least one of the impurities of the formula I or II

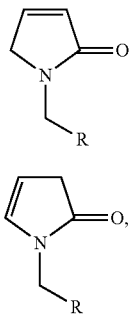

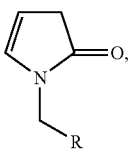

where R is hydrogen or a C1-C20-alkyl group,
c) recovering the contaminated N-alkylpyrrolidone in step b, and adding a basic compound to the recovered N-alkylpyrrolidone to form a mixture, wherein the temperature of the mixture is increased to at least 80° C. not more than 20 minutes after addition of the basic compound,
d) distilling the N-alkylpyrrolidone from the mixture to provide a purified N-alkylpyrrolidone, and
e) recycling the purified N-alkylpyrrolidone as solvent for the production of electrodes for the lithium ion accumulators, and wherein the contaminated N-alkylpyrrolidone comprises 100 parts by weight of N-alkylpyrrolidone, from 0.0005 to 2.5 parts by weight of organic compounds of the formulae I to XII as impurities, and from 0.1 to 100 parts by weight of water

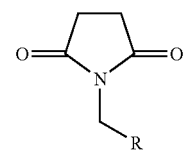

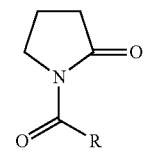

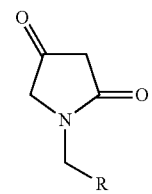

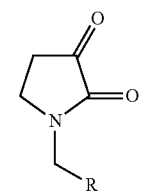

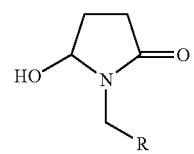

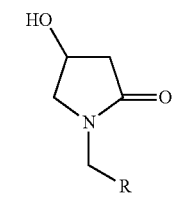

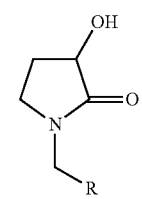

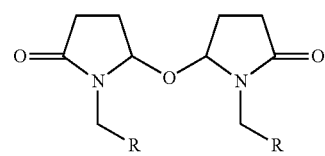

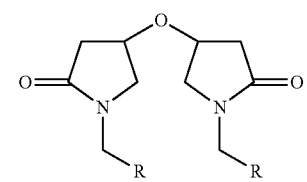

-continued

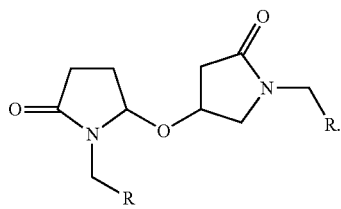

XII

2. The process according to claim 1, wherein the N-alkylpyrrolidone is N-methylpyrrolidone.

3. The process according to claim 1, wherein the adding of the basic compound includes adding from 0.01 to 10 parts by weight of the basic compound per 100 parts by weight of N-alkylpyrrolidone.

4. The process according to claim 1, wherein the temperature of the mixture is at least 100° C. not more than 5 minutes after addition of the basic compound.

5. The process according to claim 1, wherein the basic compound is added during the distillation.

6. The process according to claim 5, wherein the distillation is carried out in the absence of oxygen.

7. The process according to claim 1, wherein the purified N-alkylpyrrolidone comprises less than 0.05 part by weight of water, less than 0.5 part by weight of compounds of the formulae III and XII, and less than 0.01 part by weight of compounds of the formulae I and II, based on 100 parts by weight of the purified N-alkylpyrrolidone.

8. The process according to claim 1, wherein the purified N-alkylpyrrolidone comprises less than 0.03 part by weight of water, and less than 0.1 part by weight of compounds of the formulae III and XII, based on 100 parts by weight of the purified N-alkylpyrrolidone.

* * * * *